United States Patent
Berry

(10) Patent No.: US 12,138,175 B2
(45) Date of Patent: Nov. 12, 2024

(54) LORDOTIC EXPANDING IMPLANT

(71) Applicant: Bret Michael Berry, Tallahassee, FL (US)

(72) Inventor: Bret Michael Berry, Tallahassee, FL (US)

(*) Notice: Subject to any disclaimer, the term of this patent is extended or adjusted under 35 U.S.C. 154(b) by 0 days.

(21) Appl. No.: 18/118,469

(22) Filed: Mar. 7, 2023

(65) Prior Publication Data

US 2024/0299180 A1 Sep. 12, 2024

(51) Int. Cl.
*A61F 2/44* (2006.01)

(52) U.S. Cl.
CPC ....... *A61F 2/44* (2013.01); *A61F 2310/00011* (2013.01); *A61F 2310/00179* (2013.01)

(58) Field of Classification Search
CPC ...... A61F 2/4455; A61F 2/446; A61F 2/4465; A61F 2/447; A61F 2002/30471; A61F 2002/30538; A61F 2002/30507; A61F 2002/30545; A61F 2002/30553

See application file for complete search history.

(56) References Cited

U.S. PATENT DOCUMENTS

| | | | | |
|---|---|---|---|---|
| 10,137,007 B2* | 11/2018 | Dewey | .............. | A61F 2/4455 |
| 10,182,922 B2* | 1/2019 | Nichols | .............. | A61B 17/56 |
| 10,238,503 B2* | 3/2019 | Branch | .............. | A61F 2/4601 |
| 10,363,142 B2 | 7/2019 | McClintock | .......... | A61F 2/4455 |
| 11,065,127 B1* | 7/2021 | Lentner | .............. | A61F 2/4425 |
| 11,285,014 B1* | 3/2022 | Josse | .............. | A61F 2/4455 |
| 11,376,134 B1* | 7/2022 | Dewey | .............. | A61F 2/4455 |
| 2013/0197642 A1* | 8/2013 | Ernst | .............. | A61F 2/442 623/17.16 |
| 2014/0114420 A1* | 4/2014 | Robinson | .............. | A61F 2/447 623/17.16 |
| 2015/0272743 A1* | 10/2015 | Jimenez | .............. | A61F 2/447 623/17.16 |
| 2016/0262907 A1* | 9/2016 | Jimenez | .............. | A61F 2/447 |

* cited by examiner

Primary Examiner — Ellen C Hammond
Assistant Examiner — Holly Joanna Lane
(74) Attorney, Agent, or Firm — McCarter & English, LLP; James M. Smedley; Alex Korona

(57) ABSTRACT

An interbody implant is provided that may expand lordotically and has an additional plate to secure the implant and its expansion.

19 Claims, 12 Drawing Sheets

LORDOTIC EXPANDING IMPLANT

TECHNICAL FIELD

The present disclosure generally relates to interbody devices, and more particularly to interbody lordotic expanding implants.

BACKGROUND

There are many expandable devices for interbody implantation. Expandable implants are desirable because they minimize the access wound needed for surgery, yet while still getting the resulting spinal correction and fusion. Additionally, since patient anatomy can vary greatly from patient to patient, an expandable device can better accommodate and adapt to the anatomy for a more precise fit, which should lead to better stabilization and fusion. Lordosis is defined as an excessive inward curve of the spine. It differs from the spine's normal curves at the cervical, thoracic, and lumbar regions, which are, to a degree, either kyphotic (near the neck) or lordotic (closer to the low back). The spine's natural curves position the head over the pelvis and work as shock absorbers to distribute mechanical stress during movement. One of the biggest drawbacks is their strength. The many small components needed to create the expansion device can greatly reduce strength and lead to failure.

Accordingly, it is an object of the present invention to relatively small lordotic expanding implant with superior strength.

SUMMARY OF THE INVENTION

The present invention may include a lordotic assembly comprising an expandable assembly made from implantable material. The present invention may further include a U-shaped body with a distal wall and at least one end plate, wherein the body has solid and porous portions. The distal wall has a plurality of pivot apertures located superior and inferior within the distal wall that attaches to the endplates allowing the endplates to pivot. The at least one endplate has an outer surface defined by a set of teeth to provide fixation to a vertebral body endplate. The present invention may also include a drive screw and drive block and at least one arm assembly with retaining means and a retaining plate attached to the expandable assembly with a locking means to hold the expandable assembly in a desired location.

DETAILED DESCRIPTION

Figure 1:
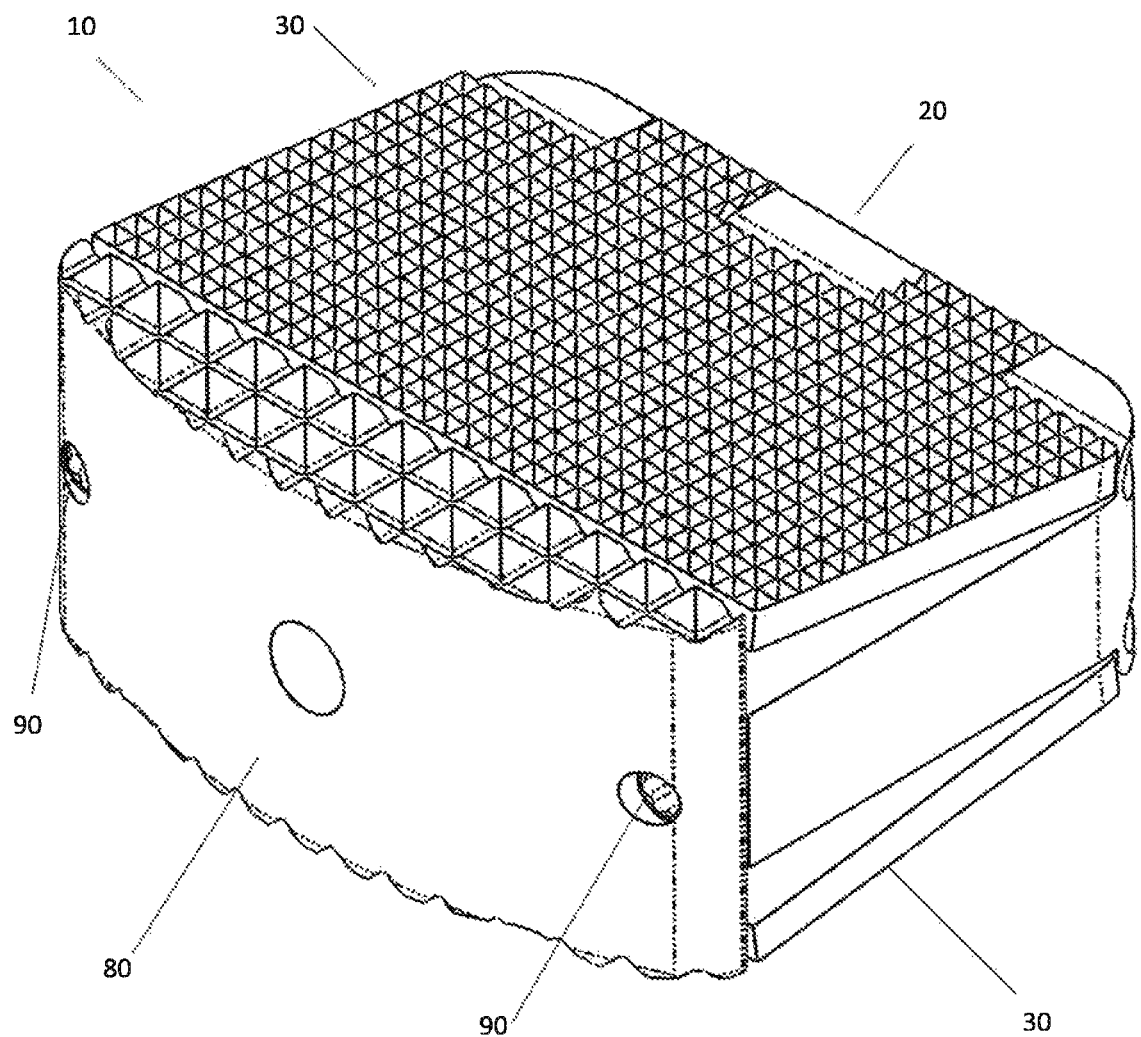
FIG. 1—Perspective view of the final assembled device.
Figure 2:
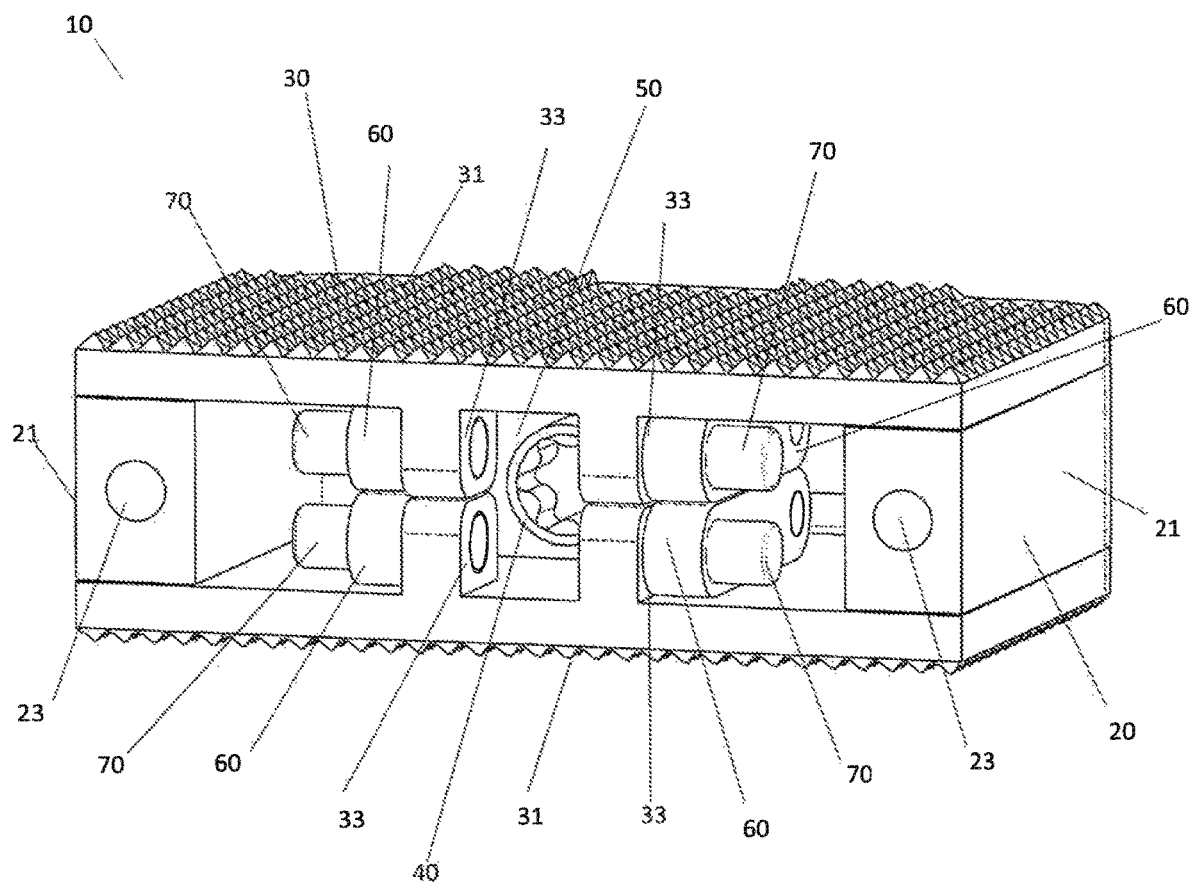
FIG. 2—Perspective view of unexpanded expandable assembly.
Figure 3:
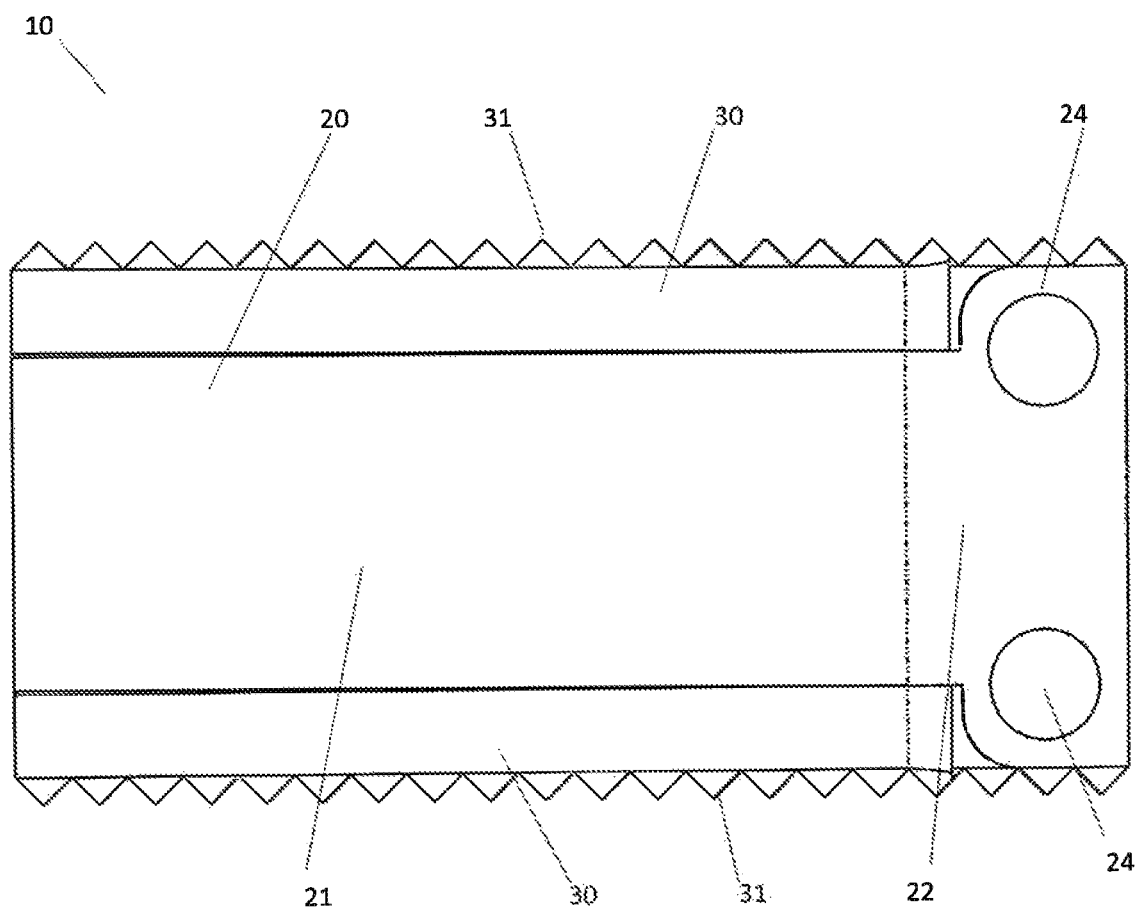
FIG. 3—Lateral view of unexpanded expandable assembly.
Figure 4:
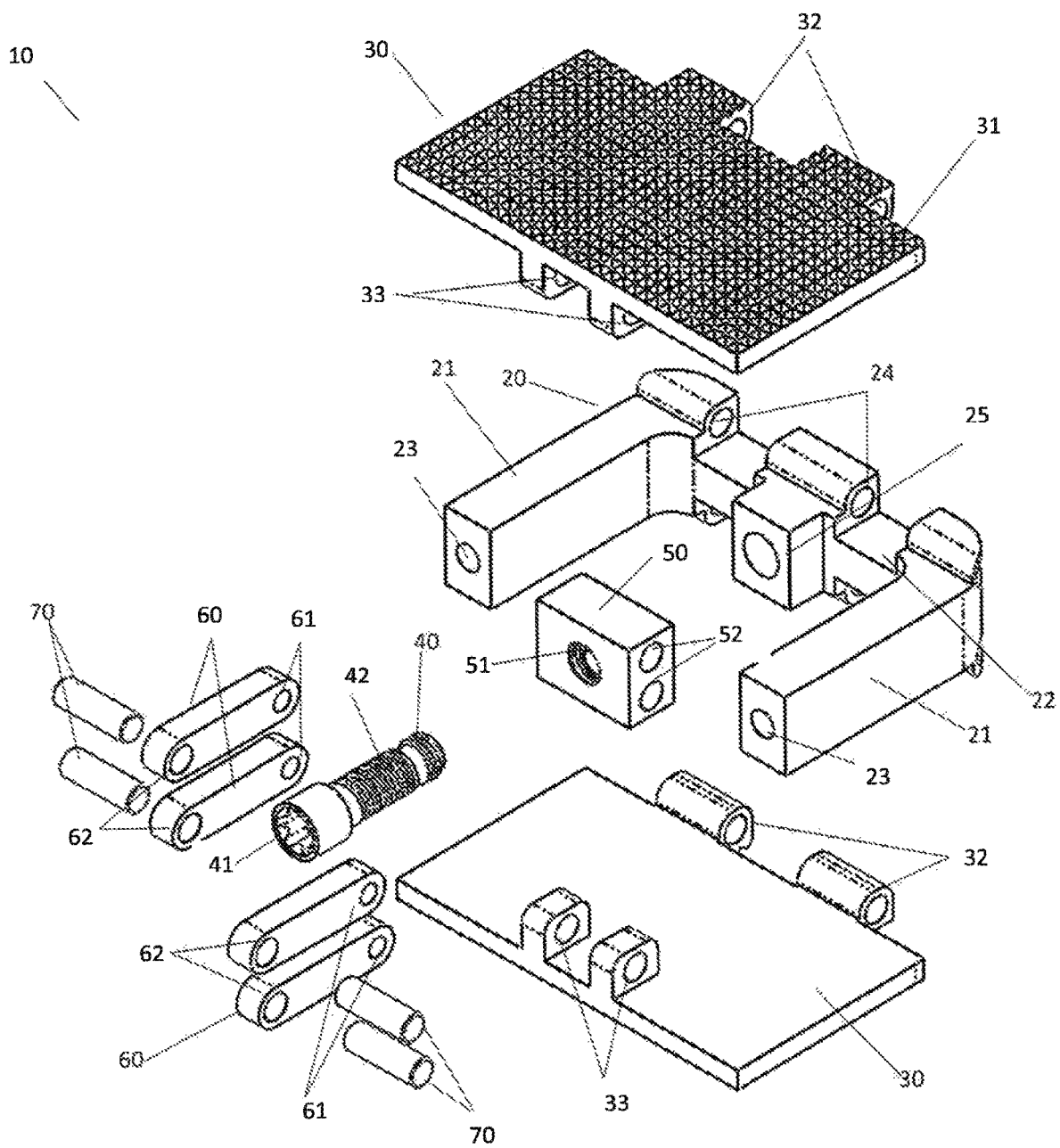
FIG. 4—Exploded view of expandable assembly.
Figure 5:
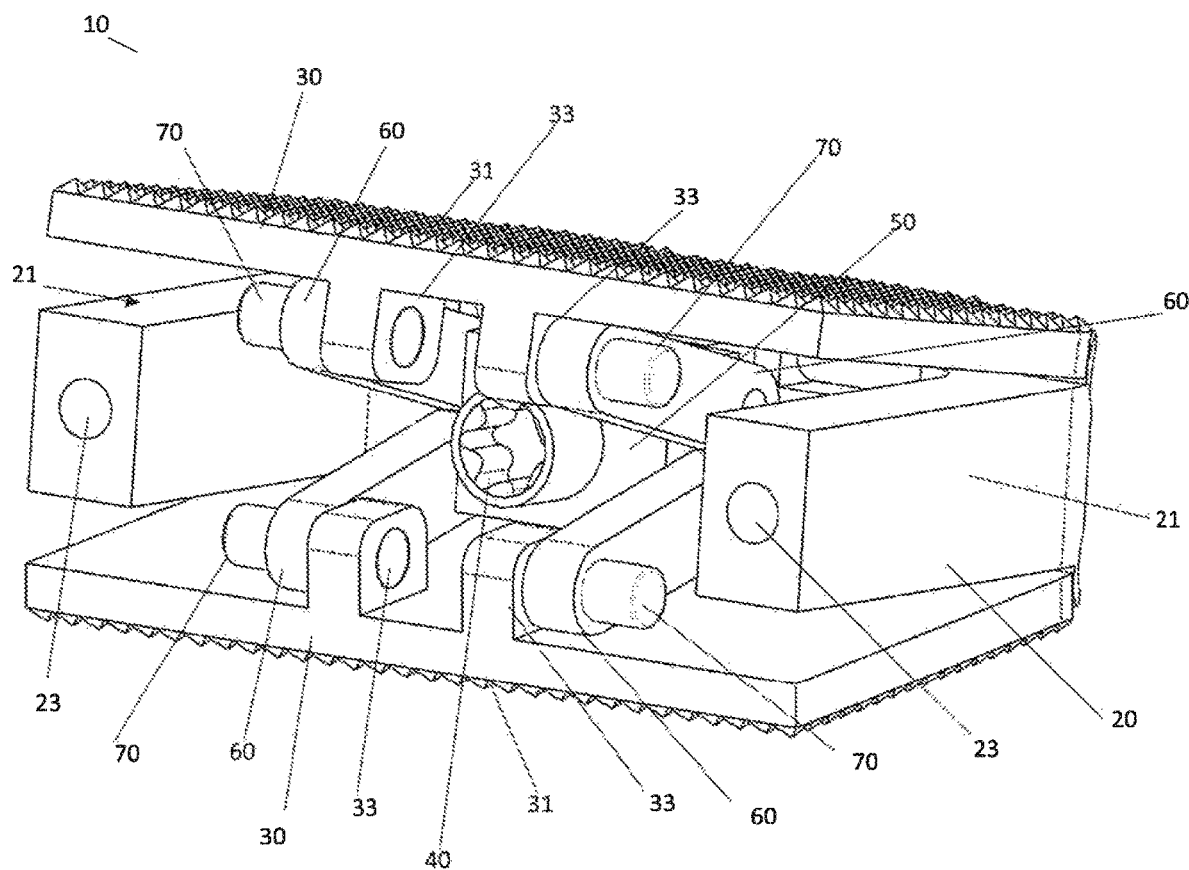
FIG. 5—Perspective view of expandable assembly.
Figure 6:
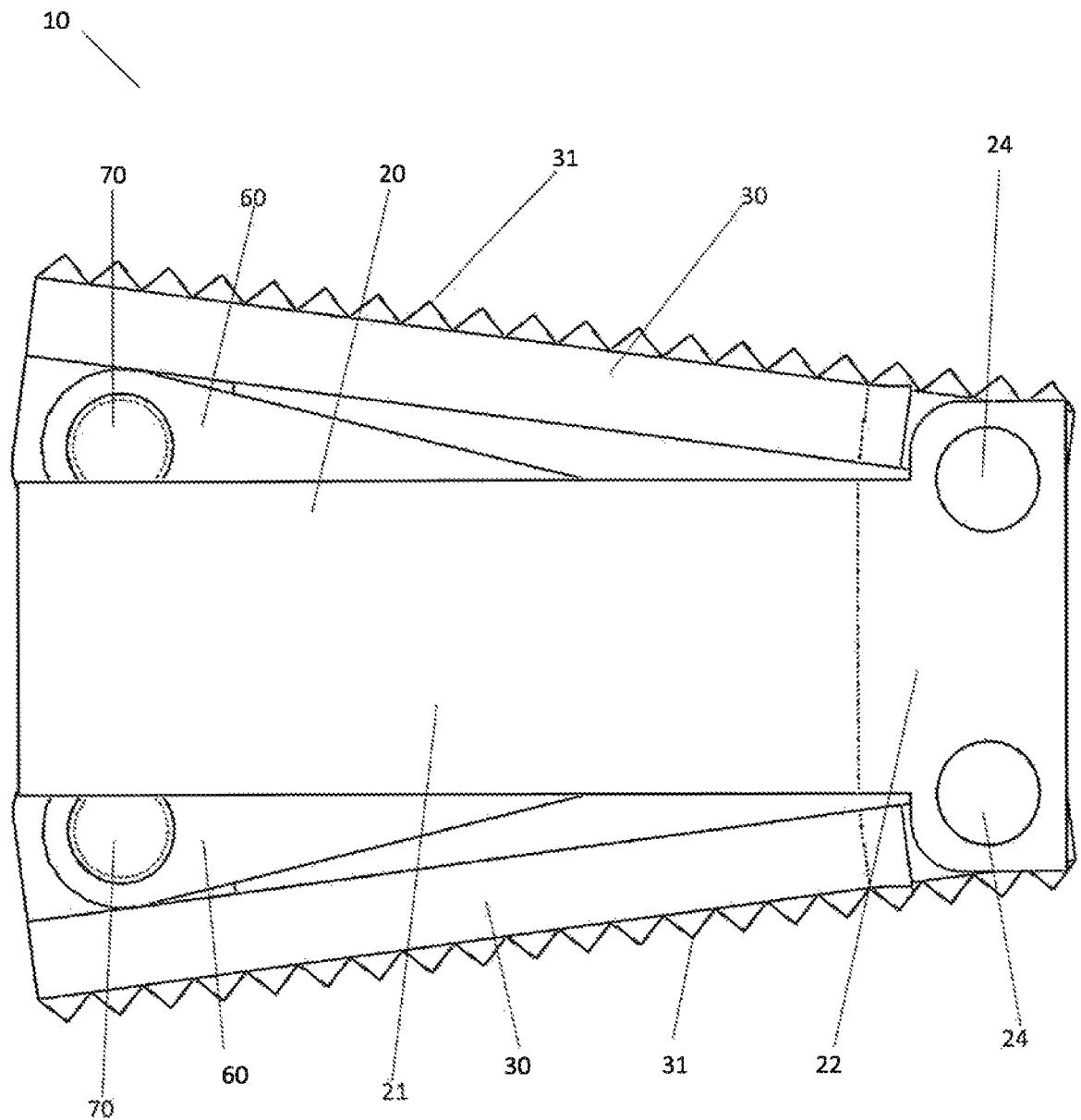
FIG. 6—Lateral view expanded expandable assembly.
Figure 7:
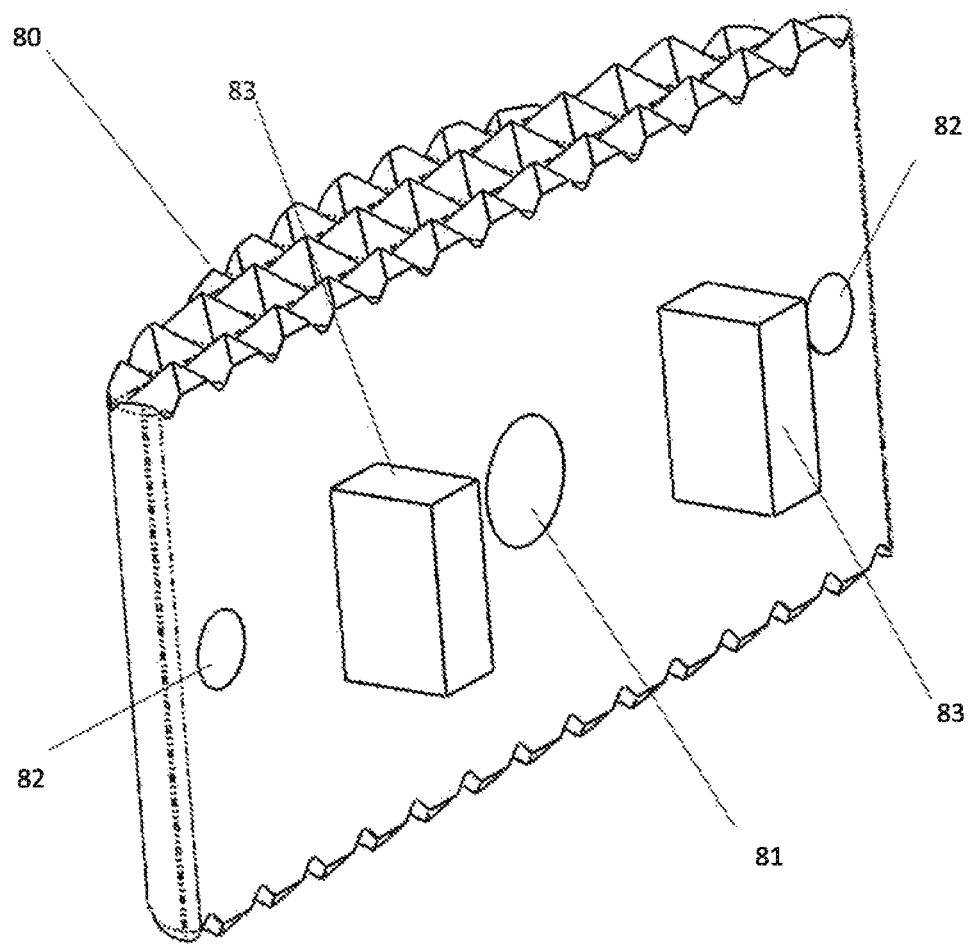
FIG. 7—Distal view of plate.
Figure 8:
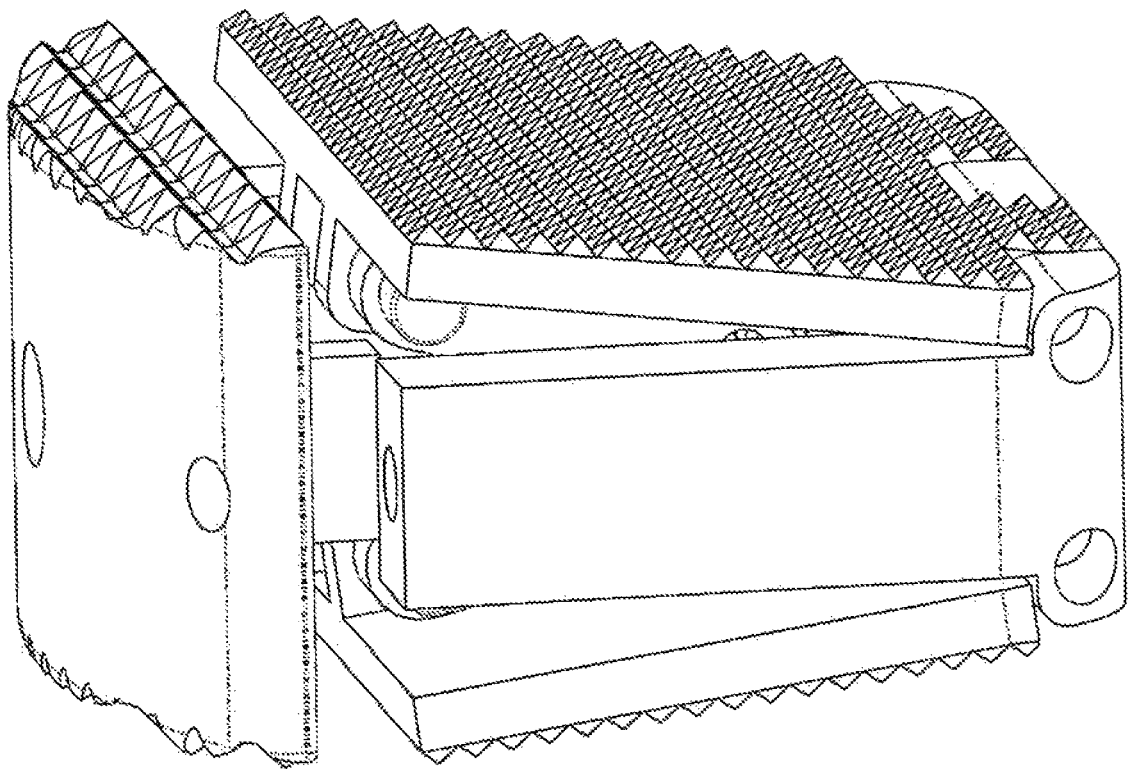
FIG. 8—Perspective view of plate being placed into expanded expandable assembly.
Figure 9:
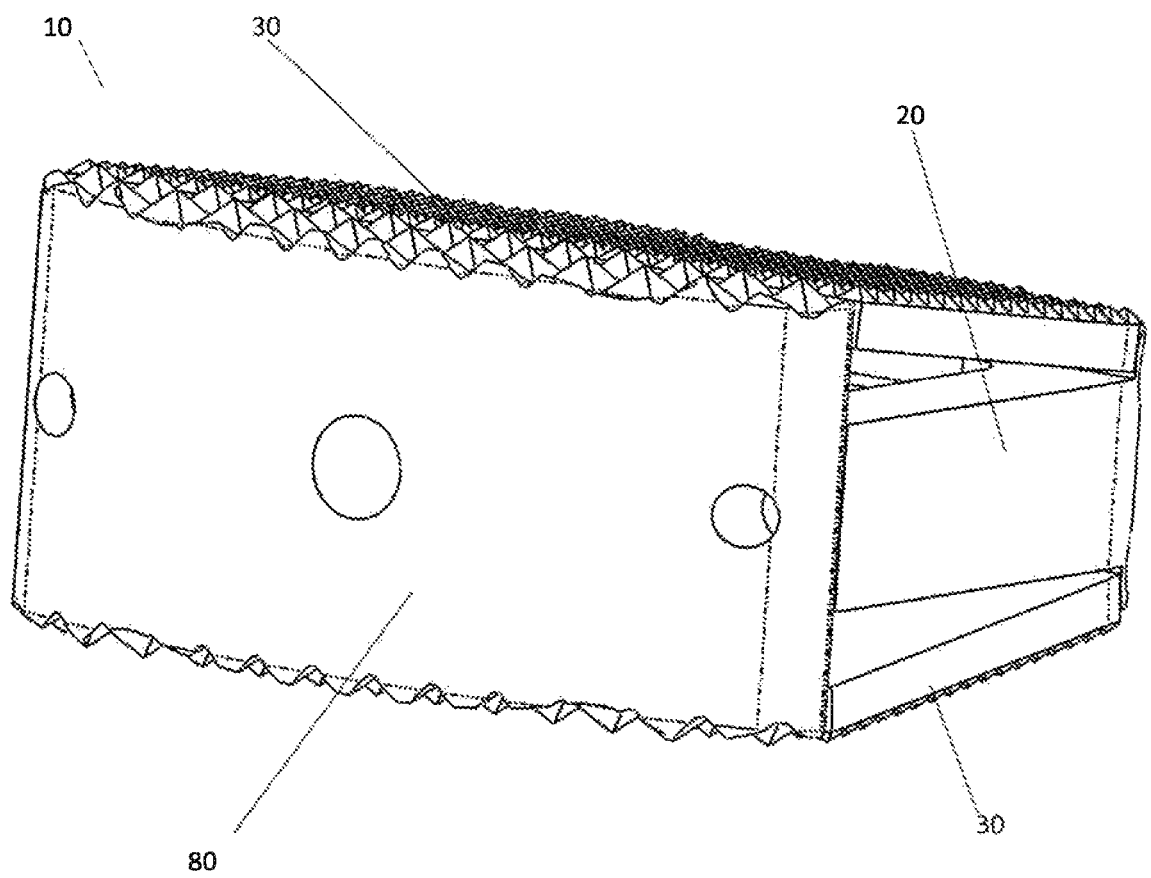
FIG. 9—Perspective view of expanded expandable assembly with plate.
Figure 10:
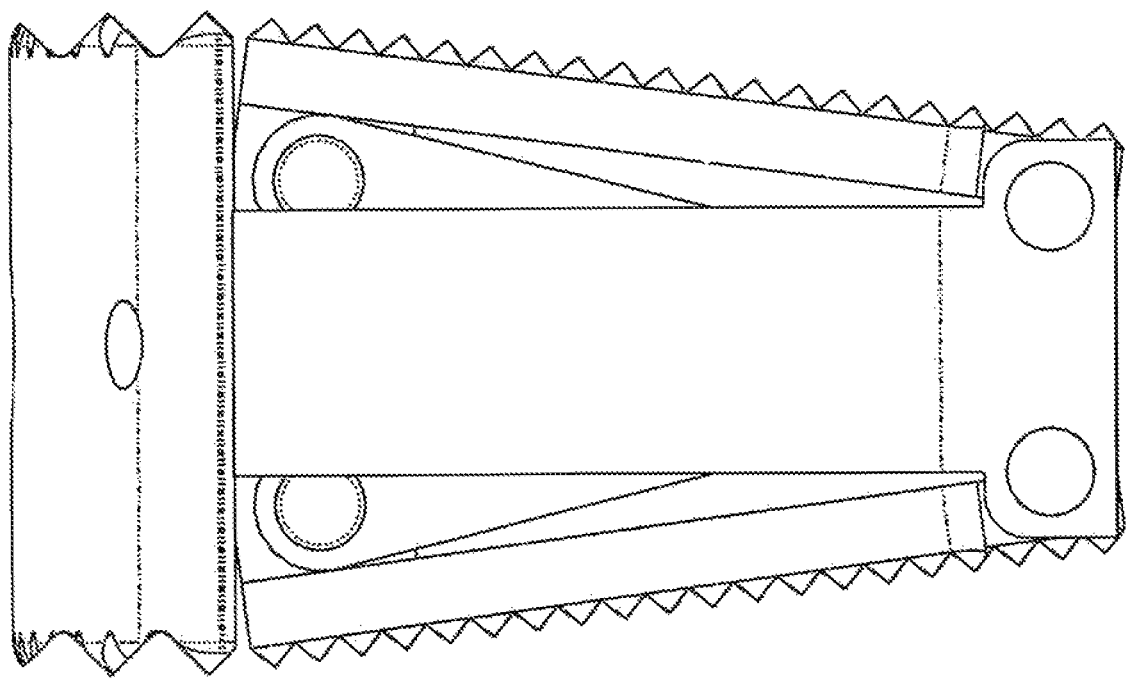
FIG. 10—Lateral view of expanded expandable assembly with plate.
Figure 11:
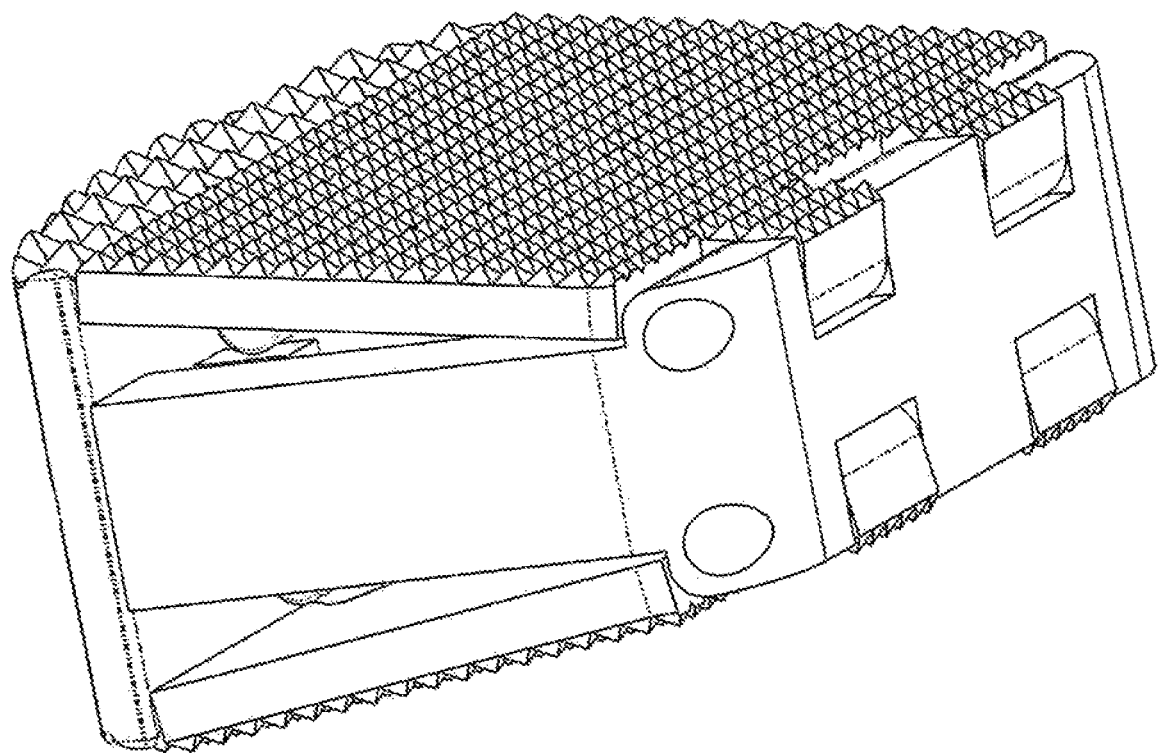
FIG. 11—Distal view of expanded expandable assembly with plate.
Figure 12:
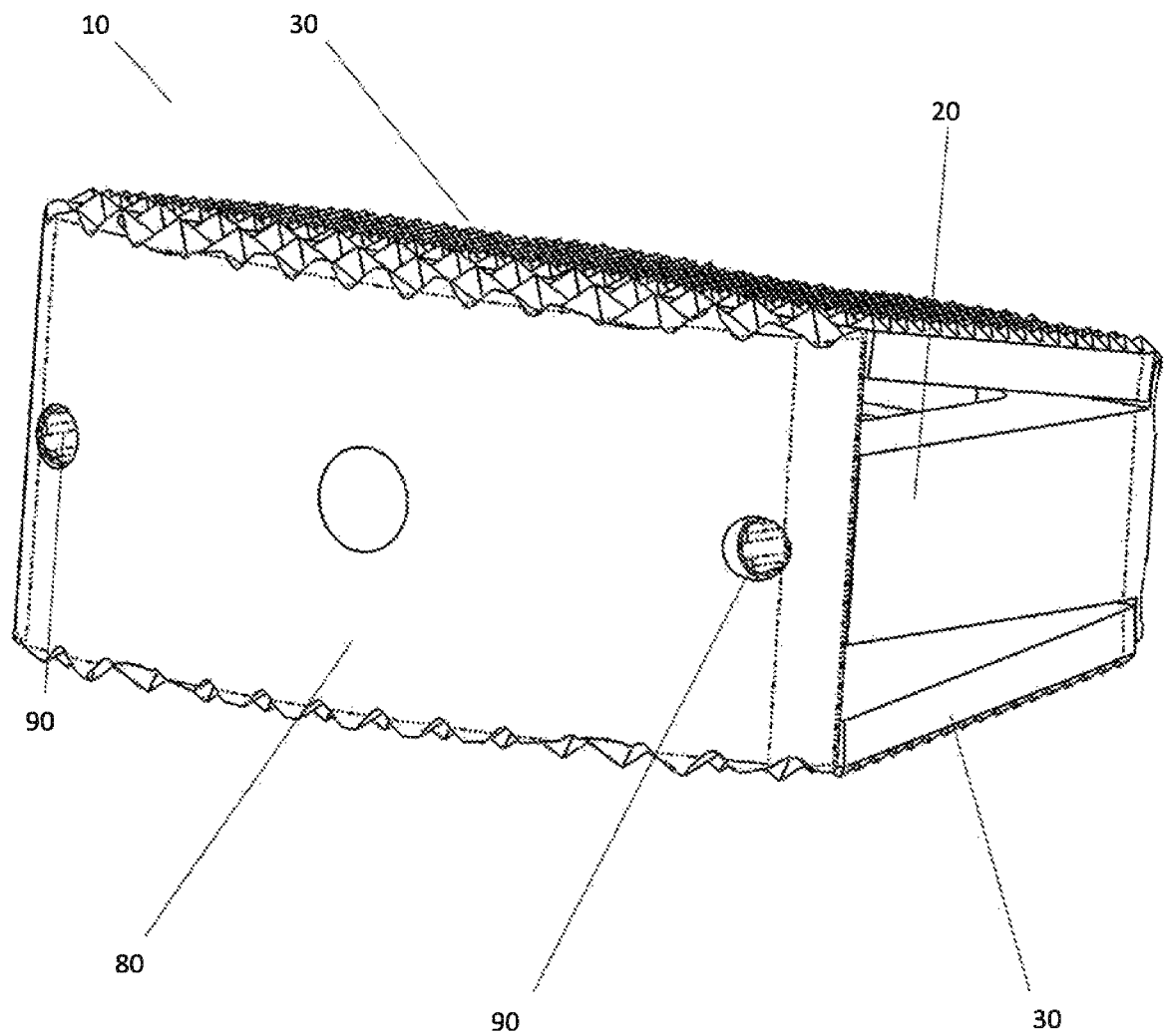
FIG. 12—Perspective view of expanded expandable assembly with plate and locking screws.

As shown in FIGS. 1-12, the preferred embodiment expandable assembly 10 includes body 20 and at least one endplate 30, drive screw 40, drive block 50, arms 60, and retaining means 70. Retaining plate 80 may be attached to expandable assembly 10 with locking means 90 in order to hold the expansion plate in place.

Body 20 may be a "U" shape in structure, which may be made of an implantable material such as metal, ceramic, or polymer, and may have solid or porous portions. On the distal wall 22 of body 20 are located pivot apertures 24. There are a set of pivot apertures 24 for each endplate 30 to attach to and allows the endplates 30 to pivot about them.

Generally pivot apertures 24 are superior and inferior on distal wall 22. Along the A-P axis of distal wall 22 may be drive aperture 25, which holds drive screw 40, allowing drive screw 40 to spin within it, but retaining drive screw 40 and preventing it from moving forwards or backwards.

On the anterior face of sidewalls 21 of body 20 are attachment apertures 23 for retaining plate 80. Endplates 30 may have an outer surface defined by a set of teeth 31. Teeth 31 are designed to provide fixation to the vertebral endplate. On the distal edge of endplate 30 is distal aperture 32. Distal aperture 32 mates with pivot aperture 24 of body 20 to allow endplate 30 to hinge in reference to body 20. On the proximal edge of endplate 30 is at least one front aperture 33. The front aperture 33 mates with arms 60.

Drive screw 40 mates into drive aperture 25 of body 20. Drive screw 40 consists of threads 42 and drive feature 41. Drive feature 41 faces proximally to allow the surgeon to manipulate drive screw 40. Threads 42 mate with drive block 50.

Drive block 50 may have threaded aperture 51 extending from the proximal to distal faces. Drive screw 40 threads through threaded aperture 51. As drive screw 40 is rotated, drive block 50 moves axially along drive screw 40. In the unexpanded state of expandable assembly 10, drive block 50 is located distally. On the lateral faces of drive block 50 are pivot apertures 52, one pivot aperture 52 per arm 60.

Arms 60 extend from drive block 50 to endplate 30. The block connecting aperture 61 of arm 60 pivots about pivot aperture 52 of drive block 50. Similarly, the endplate connecting aperture 62 of arm 60 pivots about front aperture 33 of endplate 30. As drive block 50 moves forward along drive screw 40, arm 60 also moves forward, thereby forcing the proximal edge of endplate 30 outward. As the distal end of endplate 30 is hinged on the distal wall 22 of body 20, the endplates 30 alter the lordotic angle of the expandable assembly 10. Retaining means 70 hold arm 60 to the front aperture 33 extend out beyond arms 60.

Once endplates 30 of expandable assembly 10 is placed in the desired lordotic angle, retaining plate 80 is put into place. Retaining plate 80 may have an inserter aperture 81 to allow the surgeon to place and manipulate plate 80. Additionally, inserter aperture 81 is large enough to allow drive screw 40 to be accessed through it. Extending proximal to distal on the lateral portions of plate 80 locking apertures 82. Locking apertures 82 align with attachment apertures 23 of body 20. Extending from the distal face of retaining plate 80 are fixation tabs 83. Fixation tabs 83 of plate 80 are aligned with retaining means 70 where they extend past arms 60. Therefore, fixation tabs 83 hold expandable assembly 10 in its expanded position. Lock screws 90 are inserted through retaining plate 80, locking aperture 82 and into attachment aperture 23 of body 20, thereby locking plate 80 to body 20.

It will be apparent to those skilled in the art that various modifications and variations can be made to the disclosed apparatus, system, and method. Other embodiments will be apparent to those skilled in the art from consideration of the specification and practice of the disclosed method and apparatus. It is intended that the specification and examples be considered as exemplary only, with a true scope being indicated by the following claims.

What is claimed is:

1. A lordotic expandable implant comprising:
a body comprising,
   a wall having a top face and a bottom face, wherein the top and bottom face are each formed with one or more endplate attachment points,
   a first sidewall and second sidewall connected by the wall and extending perpendicularly from the wall such that the body has "U" shaped structure, wherein the one or more endplate attachment points are set in from the first sidewall and the second sidewall;
a first endplate and second endplate, each of the endplates being configured with one or more body attachment points and one or more drive assembly attachment points, wherein each of the one or more body attachment points are configured to attach to and hinge with one of the one or more endplate attachment points; and
a drive assembly comprising,
   a drive block, wherein the drive block moves relative to the body,
   a drive screw, wherein the drive block moves along the drive screw between the first and second sidewall, and
   a plurality of arms, wherein each of the arms has a first end attached to the drive block and a second end attached to one of the drive assembly attachment points of one of the endplates.

2. The lordotic expandable implant of claim 1, further comprising a retaining plate configured to attach to the body, wherein the retaining plate is positioned farther from the wall than the plurality of arms when the retaining plate is attached to the body.

3. The lordotic expandable implant of claim 2, wherein the retaining plate is formed with a one or more fixation tabs extending from a rear face of the retaining plate and one or more locking apertures extending through the retaining plate, the rear face of the retaining plate abutting with a front edge of each of the endplates when the retaining plate is attached to the body.

4. The lordotic expandable implant of claim 3, wherein each of the sidewalls has a front face configured with an attachment aperture that aligns with one of the locking apertures of the retaining plate, the front face of each of the sidewalls extending to the front edge of the endplates when the endplates are in an unexpanded configuration.

5. The lordotic expandable implant of claim 3, wherein the fixation tabs are configured to abut with one or more components of the drive assembly to hold the endplates in an expanded position.

6. The lordotic expandable implant of claim 1, wherein each of the endplate attachment points comprises:
   a notch formed in the top face or the bottom face of the wall, wherein the notch is configured to receive one of the body attachment points of one of the endplates; and
   a pivot aperture on each side of the notch to provide a hinge point for the body attachment point of the endplate, wherein the body attachment point of the endplate is received between the pivot apertures.

7. The lordotic expandable implant of claim 1, wherein each of the body attachment points extends from a rear edge of one of the endplates and each body attachment point of the body attachment points having a top surface that is continuous with a top surface of the endplate from which the body attach point extends.

8. A lordotic expandable implant comprising:
a body comprising,
   a wall connecting between a first sidewall and a second sidewall that extend perpendicular to the wall, wherein the wall has a top face and a bottom face and each of the sidewalls have a front face that is at a distal end of each of the sidewalls relative to the wall,
   one or more endplate attachment points, wherein each of the end plate attachment points is a notch formed in the top face or the bottom face of the wall, and
   an attachment aperture formed on the front face of each of the sidewalls;
a first endplate and second endplate, each of the endplates being configured with one or more body attachment points and one or more drive assembly attachment points, wherein each of the one or more body attachment points are configured to attach to the wall of the body at one of the one or more endplate attachment points;
a drive assembly comprising,
   a drive screw,
   a drive block, and
   a plurality of arms, wherein each of the arms has a first end attached to the drive block and a second end attached to one of the drive assembly attachment points of one of the endplates; and
a retaining plate configured to attach to the body via the attachment aperture on each of the sidewalls.

9. The lordotic expandable implant of claim 8, wherein the retaining plate is formed with a one or more fixation tabs extending from a rear face of the retaining plate and one or more locking apertures extending through the retaining plate.

10. The lordotic expandable implant of claim 9, wherein the fixation tabs are configured to abut with one or more components of the drive assembly to hold the endplates in an expanded position.

11. The lordotic expandable implant of claim 8, wherein the retaining plate covers all of a front face of the lordotic expandable implant when the endplates are in an expanded position.

12. The lordotic expandable implant, of claim 8, wherein the body attachment points extend from a rear edge of each of the endplates and the drive assembly attachment points extend from an inner surface of each of the endplates.

13. The lordotic expandable implant of claim 2, wherein the retaining plate covers all of a front face of the lordotic expandable implant when the endplates are in an expanded position.

14. The lordotic expandable implant of claim 5, wherein retaining pins attach the arms to the drive assembly attachment points and the retaining pins extend beyond the arms and the drive assembly attachment points to abut the fixation tabs to hold the endplates in the expanded position.

15. The lordotic expandable implant of claim 1, wherein the drive block moves along the drive screw between the plurality of arms.

16. The lordotic expandable implant of claim 1, wherein the drive block is formed with a threaded aperture through its center that is configured to receive the drive screw and wherein the drive block further comprises at least one arm attachment point formed on each lateral face.

17. The lordotic expandable implant of claim 1, wherein the drive block is configured to move away from the wall when the drive screw is rotated in a first direction.

18. The lordotic expandable implant of claim 1, wherein the wall has an inner face that is formed with a drive aperture configured to receive a first end of the drive screw to enable the drive screw to rotate within the drive aperture but prevent the drive screw from moving forwards or backwards.

19. A lordotic expandable implant comprising:
- a body comprising a wall connecting between a first sidewall and a second sidewall that extend perpendicular to the wall to form a to provide a "U" shaped structure, wherein the wall has a top face and a bottom face each formed with one or more notches that are each set between a pair of pivot apertures and each of the sidewalls have a front face configured with an attachment aperture;
- a first endplate and second endplate, each of the endplates being configured with one or more body attachment points extending from a rear edge of each of the endplates and one or more drive assembly attachment points each extending from an inner surface of each of the endplates, wherein each of the one or more body attachment points are configured to pivot between one of the pairs of pivot apertures;
- a drive assembly comprising,
    - a drive screw, wherein the wall is formed with a drive aperture configured to receive a first end of the drive screw to enable the drive screw to rotate within the drive aperture but prevent the drive screw from moving forwards or backwards,
    - a drive block, and
    - a plurality of arms, wherein each of the arms has a first end attached to the drive block and a second end attached to one of the drive assembly attachment points of one of the endplates; and
- a retaining plate configured to attach to the body via the attachment aperture on each of the sidewalls, wherein the retaining plate is formed with a one or more fixation tabs extending from a rear face of the retaining plate and one or more locking apertures extending through the retaining plate.

* * * * *